United States Patent [19]

How

[11] Patent Number: 4,552,707
[45] Date of Patent: Nov. 12, 1985

[54] SYNTHETIC VASCULAR GRAFTS, AND METHODS OF MANUFACTURING SUCH GRAFTS

[75] Inventor: Thien V. How, Woolton, England

[73] Assignees: Ethicon Inc., Somerville, N.J.; The University of Liverpool, Liverpool, England

[21] Appl. No.: 492,864

[22] Filed: May 9, 1983

[30] Foreign Application Priority Data

Jun. 2, 1982 [GB] United Kingdom ............... 8216066

[51] Int. Cl.$^4$ ................................................. B29C 9/00
[52] U.S. Cl. ........................................... 264/24; 264/8;
264/40.7; 264/103; 264/121; 264/209.2;
264/309; 264/310
[58] Field of Search ............... 264/8, 24, 40.7, 121,
264/209.2, 309, 310, 103, 258

[56] References Cited

U.S. PATENT DOCUMENTS

| | | | |
|---|---|---|---|
| 3,280,229 | 10/1966 | Simons | 264/24 |
| 3,673,296 | 6/1972 | Timko | 264/310 |
| 3,723,244 | 3/1973 | Breillatt, Jr. | 264/311 |
| 3,775,061 | 11/1973 | Glass | 264/24 |
| 4,043,331 | 8/1977 | Martin et al. | 264/24 |
| 4,143,196 | 3/1979 | Simm et al. | 264/24 |
| 4,218,410 | 8/1980 | Stephan et al. | 264/8 |
| 4,223,101 | 9/1980 | Fine et al. | 264/24 |
| 4,230,650 | 10/1980 | Guignard | 425/174.8 |
| 4,294,791 | 10/1981 | Nouda et al. | 264/40.7 |
| 4,323,525 | 4/1982 | Bornat | 264/24 |
| 4,345,414 | 8/1982 | Bornat et al. | 264/24 |
| 4,394,332 | 7/1983 | Raman et al. | 264/8 |
| 4,424,177 | 1/1984 | Immel | 264/24 |

Primary Examiner—Jeffery Thurlow
Assistant Examiner—Patrick Dailey
Attorney, Agent, or Firm—Robert L. Minier

[57] ABSTRACT

A synthetic vascular graft is made by electrostatically spinning an organic polymeric material or a precursor thereof and collecting the spun fibres on a rotating mandrel (13), the method comprising the step of controlling the speed of rotation of the mandrel (13) such that a desired degree of anisotropy is present in the synthetic vascular graft.

1 Claim, 5 Drawing Figures

SYNTHETIC VASCULAR GRAFTS, AND METHODS OF MANUFACTURING SUCH GRAFTS

The invention relates to synthetic vascular grafts and their manufacture.

It has been proposed to make synthetic vascular grafts by an electrostatic spinning process, for example, as set out in a paper by Annis et al in 1978 (trans. Am. Soc. Intern. Organs). In such a process, a fibre forming organic polymeric material, such as polyurethane, in solution is discharged from one or more traversing nozzles towards an electrostatically charged mandrel. Fibres of the polymer material are drawn to and collected on the mandrel to produce a fibrous tube. The microstructure of the fibrous material produced during electrostatic spinning is also described in the Annis et al paper.

Natural arteries are in general anisotropic, and the degree of anisotropy and the elastic moduli of the arteries increase with the distance from the heart, with the exception of coronary arteries. The aorta is, however, approximately isotropic. Studies on arterial grafts have hitherto concentrated on clinical and pathological considerations; it is the aim of this invention to be able to produce synthetic vascular grafts having desired anisotropic properties.

According to the invention there is provided a method of manufacturing a synthetic vascular graft by electrostatically spinning an organic polymeric material or a precursor thereof and collecting the spun fibres on a rotating mandrel, which method comprises the step of controlling the speed of rotation of the mandrel such that a desired degree of anisotropy is present in the synthetic vascular graft.

According to a further aspect of the invention there is provided apparatus for performing the method according to the invention which apparatus comprises a mandrel, means for rotating the mandrel, means for electrostatically charging the mandrel, means for directing organic polymeric material or a precursor thereof towards the mandrel, and means for controlling the speed of rotation of the mandrel.

The speed of rotation of the mandrel may be varied between 0 and 25000 r.p.m., and preferably between 2000 r.p.m. and 20000 r.p.m.

The speed may be kept uniform during production of a particular graft, or alternatively there may be means for varying the rotational speed of the mandrel in accordance with the traverse position of the fluid directing means. In such a way a vascular graft having varying anisotropic properties along its length could be produced.

The mandrel may be charged at $-12$ kV, and may have an external diameter between 1 mm and 20 mm.

The mandrel may be tapered to form a graft having a tapering cross-section.

The invention further provides a vascular graft made by a method according to the invention.

By way of example, one embodiment of apparatus and a method according to the invention for making a vascular graft will now be described with reference to the accompanying drawings, in which:-

Figure 1:
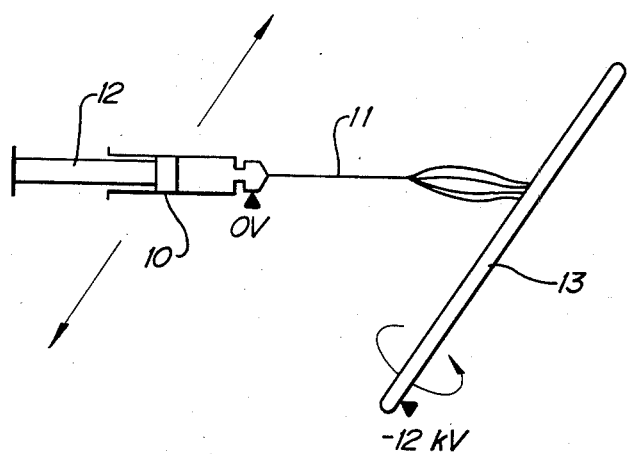
FIG. 1 is a diagrammatic illustration of electrostatic spinning apparatus.

FIG. 1 shows diagrammatically electrostatic spinning apparatus where a polymer solution is ejected from a syringe 10 through a nozzle 11, the nozzle 11 being earthed. To provide a constant flow of polymer solution through the nozzle 11, syringe piston 12 is subjected to a constant hydraulic force. The particular polymer used in the following examples was a polyurethane, and the nozzle 11 was a stainless steel needle.

Fluid from the nozzle 11 is introduced in an electrostatic field surrounding a charged mandrel 13, the mandrel being charged to $-12$ kV. The syringe 10 is supported on a traverse mechanism which translates at a constant linear speed along the length of the mandrel. The mandrel 13 is driven by an electric motor via a drive belt and the speed of rotation of the mandrel is controlled by a thyristor controller. When a droplet of the polyurethane is introduced into the electrostatic field, the droplet elongates to form a cone or jet. From the end of the jet, fine fibres of diameter in the range 1 to 2 $\mu$m are produced and are attracted onto the mandrel 13. Layers of fibres are gradually built up forming a porous and microfibrous tube.

Sample Preparation

Grafts of 10 mm internal diameter and wall thickness ranging from 0.3 mm to 0.7 mm were produced. In order to study the effect of changing the spinning process variables on their mechanical properties, three series of grafts were made under different manufacturing conditions. In each series one variable was altered while the others were kept unchanged. The following variables were altered:-

Mandrel rotation between 1500 r.p.m. and 9000 r.p.m. (grafts M1-M6).

Traverse speed between two cm per second and 40 cm per second (grafts N1-N4).

Concentration of spinning solution between 12 g % - 16.6 g % (grafts S1-S6).

The test specimens were obtained from the cylindrical graft by opening it into a flat sheet. A die cutter was used to stamp specimens in two perpendicular directions corresponding to the circumferential and longitudinal directions of the graft. A dial gauge with a resolution of 1 $\mu$m was used for thickness measurement.

Experimental Procedure and Results

An Instron Model TT-BM fitted with a 2000 g load cell was used for all the tests. The full scale load range could be changed electronically from 0-100 to 0-2000 g in 5 steps. The specimen was held in pneumatic grips operated at an air pressure of 550kNm$^{-2}$. No slippage was detected between the test specimen and the grips. The specimen was therefore assumed to deform at a rate proportional to the rate of separation of the grips provided that the end effects due to clamping were minimal. All tests were carried out on dry specimens at room temperature.

Constant Strain Tests

Figure 2:
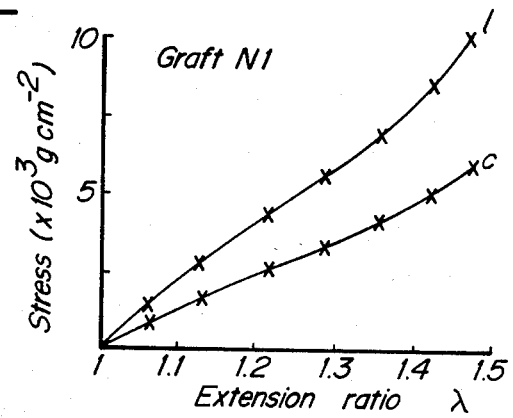
FIG. 2 shows a typical load-deformation curve for a graft sample.
Figure 3:
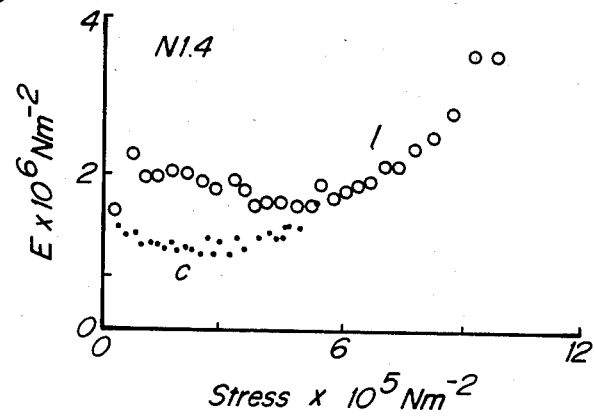
FIG. 3 is a plot of circumferential and longitudinal Young's moduli against stress.

For constant strain rate tests 10 specimens were tested from each graft — 5 longitudinal and 5 circumferential. The crosshead speed was set to 10mm/min. Each specimen was preconditioned by loading and unloading it three times. The magnitude of the deformation was 50% which was the value used in the actual measurement. The specimen was then allowed to recover for 10 minutes. Because of the small amount of set (2% at 50% elongation) the gauge length was reset before actual load-extension curve was recorded. This new length was taken at the initial length $l_o$ in the subsequent analysis. The load extension curves were digitized using a Hewlett Packard 7225B plotter and HP85 desktop computer. The data points were averaged for the five specimens and were replotted in terms of Lagrangian stress, $\sigma$, ($\sigma$=load/underformed X-sectional area) and extension ratio, $\lambda$, ($\lambda$=deformed length/initial length). FIG. 2 shows a typical load deformation curve. The anisotropic nature of the graft is apparent. A plot of the tensile modulus E ($E=d\sigma/d\lambda$) against tensile stress $\sigma$ is shown in FIG. 3. The nonlinearity of the graft is clearly seen—since for a linearly elastic material E should be independent of $\sigma$.

Effect of Electrostatic Process Variable on Tensile Properties

Figure 4:
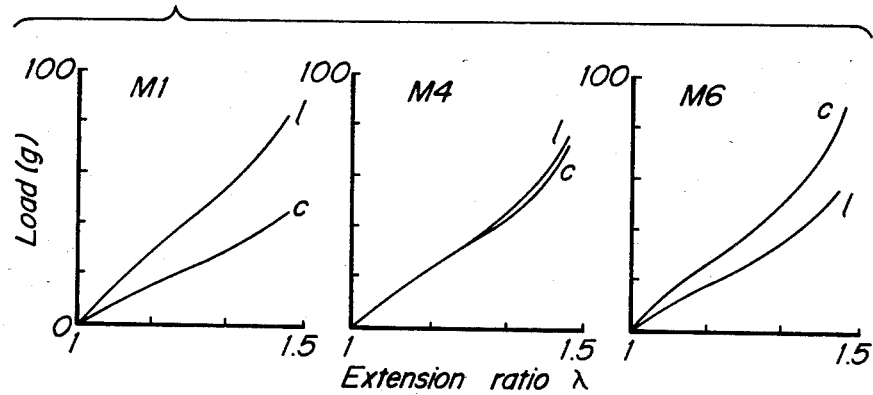
FIG. 4 shows load-extension curves at different mandrel rotation speeds.

For each graft the average longitudinal ($E_z$) and circumferential ($E_\theta$) moduli were calculated using the initial linear portion of the load deformation curves. In FIG. 4 the load-deformation curves are replotted for 3 different mandrel rotations. The change in directional properties is clearly seen.

Table 1 shows the relationship between tensile moduli, anisotropic properties and the spinning process variables.

TABLE 1

Effect of electrostatic spinning process variables on $E_\theta$ and $E_z$

1. Variable: Mandrel Rotation

| Graft | Mandrel Rotation (RPM) | $E_z$ ($\times 10^6 Nm^{-2}$) | $E_\theta$ ($\times 10^6 Nm^{-2}$) | $E_\theta/E_z$ | $E_z + E_\theta$ |
|---|---|---|---|---|---|
| M1 | 1500 | 2.10 | 1.11 | 0.53 | 3.21 |
| M2 | 3000 | 2.23 | 1.50 | 0.67 | 3.73 |
| M3 | 4000 | 1.95 | 1.57 | 0.81 | 3.52 |
| M4 | 6000 | 1.70 | 1.64 | 0.96 | 3.34 |
| M5 | 7500 | 1.53 | 1.79 | 1.17 | 3.32 |
| M6 | 9000 | 1.33 | 1.85 | 1.39 | 3.18 |

2. Variable: Traverse speed

| Graft | Traverse speed cm/s | $E_z$ ($\times 10^6 Nm^{-2}$) | $E_\theta$ ($\times 10^6 Nm^{-2}$) | $E_\theta/E_z$ | $E_z + E_\theta$ |
|---|---|---|---|---|---|
| N1 | 40 | 1.97 | 1.18 | 0.56 | 3.15 |
| N2 | 20 | 1.96 | 1.19 | 0.61 | 3.15 |
| N3 | 10 | 1.94 | 1.21 | 0.62 | 3.15 |
| N4 | 2 | 1.96 | 1.21 | 0.635 | 3.21 |

3. Variable: Spinning solution concentration

| Graft | Solution Conc. (g%) | $E_z$ ($\times 10^6 Nm^{-2}$) | $E_\theta$ ($\times 10^6 Nm^{-2}$) | $E_\theta/E_z$ | $E_z + E_\theta$ |
|---|---|---|---|---|---|
| S1 | 12 | 1.78 | 1.42 | 1.25 | 3.20 |
| S2 | 13 | 1.49 | 1.24 | 1.20 | 2.73 |
| S3 | 14 | 1.63 | 1.13 | 1.44 | 2.76 |
| S4 | 15 | 1.65 | 1.16 | 1.42 | 2.81 |
| S5 | 16 | 1.63 | 1.14 | 1.43 | 2.77 |
| S6 | 16.6 | 1.49 | 1.03 | 1.43 | 2.52 |

Values are mean of 5 measurements on different specimens from different parts of the graft.

Natural arteries are anisotropic in mechanical properties. With the exception of the coronary arteries, the degree of anisotropy and the elastic moduli increase with distance from the heart. Studies on the anistropic properties of canine femoral and carotid arteries showed that at low strain the longitudinal modulus was slightly higher than the circumferential modulus, but due to the nonlinearity of response of the arterial wall the circumferential modulus increased sharply at stresses greater than $5 \times 10^5 Nm^{-2}$ whilst the longitudinal modulus changed little. Using cylindrical segments of the carotid arteries, it has been found that at an intraluminal pressure of 80 mm of mercury, circumferential Young's modulus was $8.8 \times 10^5 Nm^{-2}$ and this increased to $1.95 \times 10^6 Nm^{-2}$ at 140 mm Hg. Over the same pressure range the longitudinal Young's modulus increased from $8.99 \times 10^5$ to $1.05 \times 10^6 Nm^{-2}$. In the coronary arteries, however, the anisotropy was reversed. It has been calculated that the incremental elastic moduli of the left coronary circumflex artery and their mean values of circumferential and longitudinal Young's modulus were $7.7 \times 10^5$ and $3.8 \times 10^6 Nm^{-2}$ respectively.

The tensile properties of synthetic grafts with knitted and woven Dacron and Teflon have been studied. Although demonstrating a large apparent longitudinal distensibility due to the presence of circular crimps, stiffness in the circumferential direction was an order of magnitude greater than that of the natural artery.

The tensile moduli of the graft samples according to the invention listed in Table 1 were the mean values calculated between an extension ratio of about 1.0 and an extension ratio of 1.09. Circumferential Young's modulus ranged from $1.03 \times 10^6$ to $1.85 \times 10^6 Nm^{-2}$ and values of longitudinal Young's modulus were between $1.33 \times 10^6$ and $2.23 \times 10^6 Nm^{-2}$. These values of Young's modulus are slightly higher than those of the natural arteries. The grafts were less anisotropic than the carotid and coronary arteries. As can be seen from Table 1, variation in the concentration of polymer solution affected the elastic moduli. There was a tendency for the circumferential modulus to decrease with the concentration but there was no definite trend in the values of the longitudinal modulus.

Figure 5:
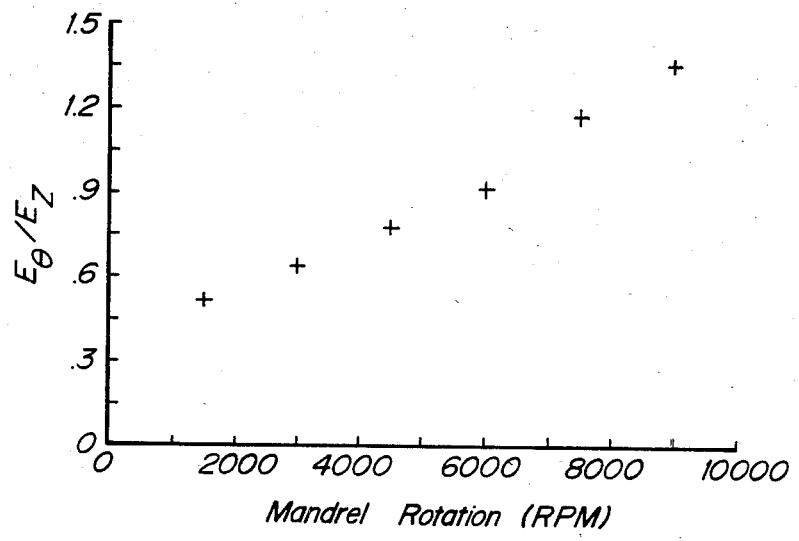
FIG. 5 shows a plot of the ratio of circumferential to longitudinal Young's moduli against mandrel rotation speed.

As can be seen in FIGS. 4 and 5, it is possible, by varying the mandrel rotation speed to control the ratio of circumferential to longitudinal modulus. At low rotation, the circumferential modulus is less than the longitudinal modulus suggesting that there is a preferential alignment of fibres in the longitudinal direction. As the speed of rotation of the mandrel increases, the tube becomes isotropic and thereafter the anisotropy reverses and the circumferential modulus becomes greater than the longitudinal modulus. The traverse speed has a small influence on anisotropy but for practical purposes its effect may be ignored.

The sample grafts were made with an internal diameter of 10 mm but it will be appreciated that variation of the mandrel rotation speed will also effect anisotropy in grafts of different diameters. The smaller the graft diameter, the less effect increasing mandrel rotation speed has on increasing the ratio between circumferential and longitudinal moduli and it is proposed to test sample grafts at mandrel rotation speeds of up to between 20000 r.p.m. and 25000 r.p.m. for diameters down to 1 mm. The useful range of vascular grafts is between 1 mm and 20 mm internal diameter, and wall thickness may vary between 0.075 mm and 2 mm.

I claim:

1. A method of manufacturing a synthetic vascular graft by electrostatically spinning an organic polymeric material or a percusor thereof and collecting the spun fibres on a rotating mandrel, which method comprises the step of varying the speed of rotation of the mandrel such that a desired degree of anisotropy is present in the synthetic vascular graft.

* * * * *